(12) United States Patent
Swamy et al.

(10) Patent No.: US 7,615,211 B2
(45) Date of Patent: Nov. 10, 2009

(54) CD70 INHIBITION FOR THE TREATMENT AND PREVENTION OF INFLAMMATORY BOWEL DISEASE

(75) Inventors: Manjunath N. Swamy, Roslindale, MA (US); Amale Laouar, Boston, MA (US)

(73) Assignee: CBR Institute for Biomedical Research, Inc., Boston, MA (US)

( * ) Notice: Subject to any disclaimer, the term of this patent is extended or adjusted under 35 U.S.C. 154(b) by 287 days.

(21) Appl. No.: 11/053,285

(22) Filed: Feb. 8, 2005

(65) Prior Publication Data

US 2005/0191299 A1 Sep. 1, 2005

Related U.S. Application Data

(60) Provisional application No. 60/543,061, filed on Feb. 9, 2004.

(51) Int. Cl.
*A61K 39/395* (2006.01)

(52) U.S. Cl. .................................................. 424/130.1

(58) Field of Classification Search ....................... None
See application file for complete search history.

(56) References Cited

U.S. PATENT DOCUMENTS

2006/0233794 A1* 10/2006 Law et al. ................ 424/144.1

OTHER PUBLICATIONS

Huang Z., Pharmacology and Therapeutics, 2000, 86: 201-215.*
Blazar et al., J. Immunol., 1996, 157: 3250-3259.*
Borst et al., Current Opinion in Immunology, 2005, 17: 275-281.*
Monika Manocha, Svend Rietdijk, Amale Laouar, Atul Bhan, Cox Terhost and Manjunath N. Swamy (2008) The FASEB Journal 22:859.10 (Abstract included).

* cited by examiner

*Primary Examiner*—Ilia Ouspenski
(74) *Attorney, Agent, or Firm*—Rissman Hendricks & Oliverio LLP

(57) ABSTRACT

Substantially purified populations of $APC^{LP}$ cells capable of expressing CD70 are described. Also described are methods for the treatment of certain diseases and medical conditions of the gastrointestinal tract, such as inflammatory bowel disease, by utilizing inhibitors of CD70 activity.

3 Claims, 12 Drawing Sheets

5X

40X

40X

SEQUENCE LISTING

<160> NUMBER OF SEQ ID NOS: 1

<210> SEQ ID NO 1
<211> LENGTH: 9
<212> TYPE: PRT
<213> ORGANISM: Mouse
<220> FEATURE:
<221> NAME/KEY: PEPTIDE
<222> LOCATION: (1)..(9)

<400> SEQUENCE: 1

Lys Ala Val Tyr Asn Phe Ala Thr Cys
1               5

CD70 INHIBITION FOR THE TREATMENT AND PREVENTION OF INFLAMMATORY BOWEL DISEASE

CROSS-REFERENCE TO RELATED APPLICATIONS

This application is based on and claims the benefit of U.S. Provisional Application No. 60/543,061, filed Feb. 9, 2004, the disclosure of which is incorporated by reference herein in its entirety.

GOVERNMENT SPONSORED RESEARCH OR DEVELOPMENT

This work was funded in whole or in part by a grant from the National Institutes of Health pursuant to grant no. NIH/NIAID 46566. The federal government may have certain rights in the invention.

BACKGROUND OF THE INVENTION

This invention relates to substantially pure, isolated populations of antigen presenting cells ("APC" cells), methods for obtaining such purified cell populations, and methods for treating diseases of the gastrointestinal tract using inhibitors of the CD70 antigen expressed on activated B cells and T lymphocytes, and in particular, a method for treating and preventing inflammatory bowel disease using CD70 inhibitors.

The intestinal immune response is different from the immune response of other organs in the body, but the basis for the distinctiveness of the intestinal immune response is not fully understood.

Lymphocytes in the intestinal mucosa possess several features that are distinct from their counterparts in the secondary lymphoid organs. It has been suggested that the activation pathways of mucosal T cells are different from those of peripheral T cells. In contrast to peripheral T cells, intestinal mucosal T cells are resistant to TCR-CD3 stimulation, but proliferate vigorously and secrete pro-inflammatory cytokines after CD2 stimulation. Similarly, intestinal mucosal T cells express distinctive adhesion molecules, and their costimulatory requirements are different than peripheral T cells. Again, for instance, the systemic administration of soluble protein antigen without adjuvant induces differentiated cytotoxic T cells in intestinal mucosa, but not in spleen and lymph nodes. Finally, transactivation of IFN-γ expression in peripheral T cells and mucosal T cells occurs through the use of different cis-regulatory elements, and requires the recruitment of different transactivating factors. One possible reason for these differences is that T cells may be stimulated with different types of antigen presenting cells in the mucosa and peripheral regions of the body.

Different subsets of dendritic cells have been identified in intestinal lymphoid organs. In addition to the myeloid dendritic cells and the lymphoid dendritic cells found in the spleen and lymph nodes, Peyer's patch and mesenteric lymph nodes also contain a novel population of dendritic cells. However, Peyer's patch dendritic cells differ from splenic and lymph node dendritic cells in their ability to induce cytokine production. For instance, in contrast to splenic dendritic cell-stimulated T cells, which produce IFN-γ, Peyer's patch dendritic cell-primed T cells secrete predominantly IL-10 and L-4. Further, after ligation of the costimulatory molecule, RANK, Peyer's patch dendritic cells produce IL-10, while splenic dendritic cells produce IL-12. Thus, while splenic dendritic cells provide a stimulatory environment, Peyer's patch dendritic cells generally provide an inhibitory environment. Given this fact, it is surprising that the intestinal mucosal T cell response to infections is more robust and more prolonged than in peripheral cells, despite an equivalent antigen load.

Dendritic cells are antigen-presenting cells found in all tissues and organs of the body. The dendritic cells present antigens for T lymphocytes, i.e., they process and present antigens, and stimulate responses from naive and memory T cells. In addition to their role in antigen presentation, dendritic cells directly communicate with non-lymph tissue and survey non-lymph tissue for an injury signal (e.g., ischemia, infection, or inflammation), or tumor growth. Once signaled, dendritic cells initiate an immune response by releasing inflammatory cytokines which trigger lymphocytes and myeloid cells. Various immunodeficiencies are thought to result from the loss of dendritic cell function.

One of the important features of dendritic cell maturation is the upregulation of costimulatory molecules. Although, as noted above, differences in cytokine induction have been described, so far no differences in the induction of costimulatory molecules have been reported between peripheral and intestinal dendritic cells. CD70 is also known to be a TNF-related costimulatory ligand. CD70 has been shown to be expressed by activated murine dendritic cells in vitro, and the persistent expression of CD70 in transgenic mice results in the activation of naïve T cells, and the expansion of effector memory cells, leading ultimately to the exhaustion of the naïve T cell pool. However, the constitutive CD70 expression by immune cells in vivo has not been reported.

Dendritic cell populations in the intestinal mucosa remain poorly characterized. Although dendritic cells from lamina propria tissue have been shown to be capable of penetrating the intestinal epithelial layer to sample luminal bacteria, no distinct dendritic cell subsets have so far been described in the lamina propria compartment.

An understanding of the immune response in the gastrointestinal tract is essential in order to develop effective treatments for intestinal diseases such as inflammatory bowel disease. Inflammatory bowel disease is a medical condition that results when cells involved in inflammation and immune response infiltrate the lining of the gastrointestinal tract. This infiltration thickens the bowel lining and interferes with liquid absorption and motility, thereby disrupting the normal functioning of the bowel.

Accordingly, it is an objective of this invention to provide methods for treating diseases of the gastrointestinal tract using inhibitors of CD70, and in particular, to methods for treating inflammatory bowel disease using such inhibitors.

It is a further objective of this invention to provide substantially pure, isolated populations of unique antigen presenting cells found in the intestinal mucosa, and methods for obtaining such purified cell populations.

SUMMARY OF THE INVENTION

According to the invention, a novel type of antigen presenting cell occurring in the lamina propria compartment, and constitutively expressing the costimulatory molecule CD70, has been identified and characterized. These cells, designated as antigen presenting lamina propria ($APC^{LP}$) cells, have been found to play a pivotal role in the expansion and differentiation of T cells in the intestinal mucosa. These novel $APC^{LP}$ cells are characterized as follows: MHC class II+, DEC205+, B220+, CD80+; CD70+, and the ability to stimulate an alloresponse. These cells are also characterized as being CD40−, CD86−, and are capable of secreting IL-12p70 constitutively.

In one embodiment, the invention includes a substantially pure, isolated population of lamina propria antigen presenting ($APC^{LP}$) cells, said cells being capable of expressing the CD70 antigen. Inhibitors of CD70, and particularly CD70 expression in $APC^{LP}$ cells, such as inhibitory antibodies and peptides, particularly monoclonal antibodies, are also encompassed by the invention.

In other embodiments, the invention includes methods for treating subjects having inflammatory conditions of the gastrointestinal tract by the administration to the subject of a pharmaceutical composition comprising a CD70 inhibitor in an amount effective to reduce or eliminate the inflammatory condition. The inflammatory condition can be, for instance, inflammatory bowel disease, and the pharmaceutical composition can include adjuvants and carriers. Prophylactic compositions incorporating CD70 inhibitors for the prevention of such conditions are also within the scope of this invention.

In further embodiments, the invention includes a method for the treatment of inflammatory bowel disease using a pharmaceutical composition including a CD70 antibody, such as a CD70 monoclonal antibody, a CD70 Ig-chimera, an siRNA molecule, or a small organic molecule.

In still further embodiments, the invention includes a method for inducing the enhancement of CD70 overexpression to augment a response by a subject to a mucosal vaccine used to treat the subject.

In yet other embodiments, the invention includes methods for identifying inhibitors of CD70 by contacting a candidate CD70 inhibitor with a preparation of $APC^{LP}$ cells, determining the response of the candidate CD70 inhibitor on the expression of CD70 by said cells, and identifying a suitable inhibitor which inhibits such expression. The candidate inhibitor can be part of a library of molecules, including antibodies, peptides, and siRNA molecules, and the screening methods can preferrably be high throughput screening assays.

The various features and advantages of the present invention will be better understood from the following specification when read in conjunction with the accompanying drawings.

DETAILED DESCRIPTION OF THE INVENTION

Figure 1A:
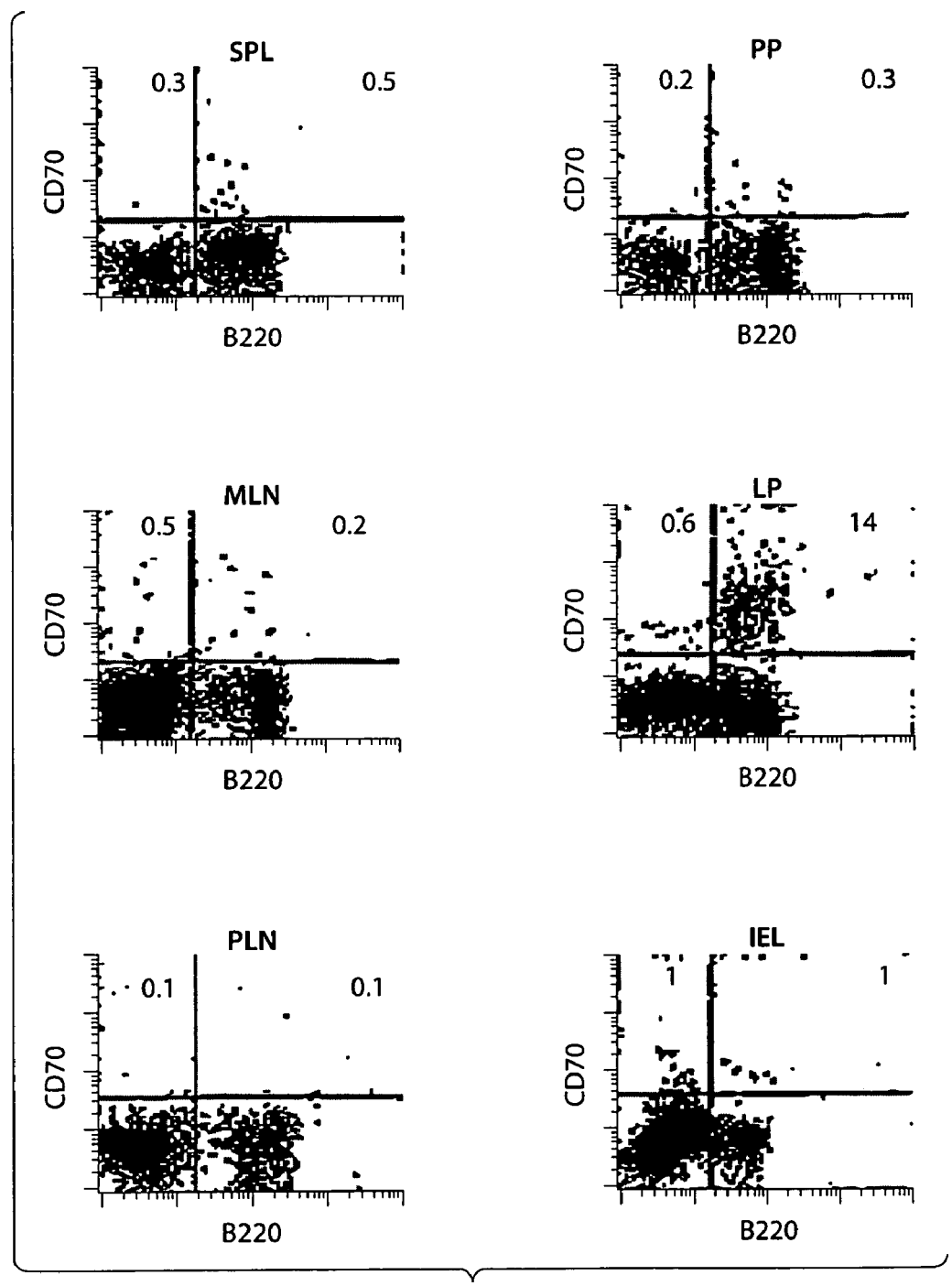
FIGS. 1A-1C illustrate the presence of a novel type of antigen presenting cell ($APC^{LP}$ cells) located in the lamina propria cell compartment.

This invention provides substantially pure populations of lamina propria antigen presenting ($APC^{LP}$) cells expressing the CD70 antigen, inhibitors for such antigens, and methods for preparing such cell populations. Also provided are treatment methods employing such inhibitors to treat disease states and medical conditions, such as for treating inflammatory diseases, and particularly inflammatory bowel disease.

As used herein, the following terms and phrases shall have the following meanings unless indicated otherwise.

A "subject", as used herein, includes mammals such as human and non-human mammals. Preferred non-human mammals include primates, pigs, rodents, rabbits, canines, felines, sheep horses, and goats. Veterinary applications are within the scope of the present application.

The abbreviation "LP", as used herein, designates the lamina propria, a mucosal tissue lying underneath the lining of the epithelium, or cells extracted from the lamina propria, as the context may dictate. This abbreviation can be used with the abbreviation "APC", which dentoes antigen presenting cells, as "$APC^{LP}$". "$APC^{LP}$" thus designates lamina propria antigen presenting cells uniquely found in the intestinal mucosa and which express the CD70 antigen.

The following are explanations of some of the other abbreviations used herein. "PP"generally denotes Peyer's patch cells or tissue. "LN" designates lymph nodes. "DC" designates dendritic cells. "LM" designates listeria monocytogene cells. "MLN" designates mesenteric lymph node cells. "CTL" designates cytotoxic T lymphocyte cells. "LT" designates lymphotoxin α.

The "treatment of" or "treating" a medical condition includes both prophylactic and therapeutic methods of treating a subject, such as the treatment of inflammatory bowel disease, and other inflammatory diseases of the gastro-intestinal tract. "Treatment" generally denotes the administration of a therapeutic agent to a subject who has a disease or disorder, a symptom of a disease or disorder, or a predisposition toward a disease or disorder, for the purpose of preventing, alleviating, relieving, reducing the symptoms of, altering, or improving the medical condition or disorder. The methods of treatment herein may be specifically modified or tailored based on a specific knowledge of the subject obtained by pharmacogenomics, and other methods for analyzing individual drug responses to therapies.

A "CD70 inhibitor" in the context of the invention generally denotes an agent that reduces or attenuates the activity level of the CD70 antigen expressed on cells including activated B cells, T lymphocyte cells, and $APC^{LP}$ cells. Such inhibition can result from a variety of events, such as the interrupted binding of the CD70 antigen to an appropriate receptor, inactivating the CD70 antigen, such as by cleavage or other modification, altering the affinity or CD70 to its ligand or receptor, preventing or reducing the expression of CD70 on a cell, expressing an abnormal or inactive CD70 antigen, or deactivating the antigen, preventing or reducing the proper conformational folding of the CD70 antigen, modifying the binding properties of the CD70 antigen, interfering with signals that are required to activate or deactivate CD70, activating the CD70 antigen at the wrong time, or interfering with other molecules required for the normal synthesis or functioning of CD70. Examples of inhibitors include inhibitory proteins, such as antibodies, inhibitory carbohydrates, inhibitory glycoproteins, chemical entities, and small molecules. Antibodies include humanized antibodies, chimeric antibodies, Fab$_2$ antibody fragments, polyclonal antibodies, and monoclonal antibodies.

A "therapeutically effective amount" of a pharmaceutical composition means that amount which is capable of treating, or at least partially preventing or reversing the symptoms of the medical condition or disease state. A therapeutically effective amount can be determined on an individual basis and is based, at least in part, on a consideration of the species of mammal, the mammal's size, the particular inhibitor used, the type of delivery system used, and the time of administration relative to the progression of the disease. A therapeutically effective amount can be determined by one of ordinary skill in the art by employing such factors and using no more than routine experimentation.

The role and activity of intestinal T cells is not completely understood by the medical community. Based on an analysis of T cells in the intra-epithelial lymphocyte cell compartment, which resemble T cell blasts in the afferent lymph in the thoracic duct, it was originally proposed that T cells are primed to antigens in Peyer's patch or mesenteric lymph nodes, and subsequently migrate to blood via the thoracic duct before accumulating in the lamina propria or the intra-epithelial lymphocyte compartment. However, mice that lack Peyer's patch, such as mice treated in utero with lymphotoxin β receptor-Ig (LTβR-Ig) fusion protein, LTβ$^{-/-}$ or LTα/LTβ$^{+/-}$ heterozygous mice, show that Peyer's patch is not indispensible for both mucosal IgA responses and for tolerance induction. Because impaired IgA responses are observed in LTα$^{-/-}$ and LTβR$^{-/-}$ mice that lack both Peyer's patch and mesenteric lymph nodes, it has been suggested that mesenteric lymph nodes might act as an alternative site for the induction of mucosal immunity. However, the mucosal IgA deficiency in LTα$^{-/-}$ mice can be reversed by the transfer of bone marrow cells from wild type mice, suggesting that the presence of LT rather than intact Peyer's patech or mesenteric lymph nodes is required for mucosal IgA production.

The site of antigen priming for T cell immunity has not previously been studied in Peyer's patch/mesenteric lymph node-deficient animals. It has been suggested that the initial priming of antigen-specific cytotoxic T lymphocytes occurs in mesenteric lymph node cells, and that these cells are further activated by antigen presentation in the intestinal epithelium. Following activation of adoptively transferred OT-1 cells (MHC class I-restricted, ovalbumin-specific TCR transgenic) by systemic administration of OVA (ovalbumin) peptide, activated cells were first observed in mesenteric lymph nodes, followed by migration into the lamina propria and the intra-epithelial lymphocyte compartment. Furthermore, in a transgenic mouse system where ovalbumin is constitutively expressed in intestinal epithelial cells, the division of adoptively transferred OT-1 cells was first seen in mesenteric lymph nodes and Peyer's patch, as evidenced by CSFE dilution. It has now been found that LTα$^{-/-}$ mice, lacking Peyer's patch and lymph nodes, are incapable of expanding T cells in the mucosa, despite possessing APC$^{LP}$ cells that are capable of providing a second stimulation. Therefore, it is reasonable to conclude that although T cells are primed in the Peyer's patch and lymph nodes, the site for major T cell expansion after oral infection is the intestinal mucosa itself.

Several subsets of mouse and human dendirtitc cells are known, based on the phenotype and function of such cells. Mouse spleen and lymph nodes contain at least 3 populations of dendritic cells: 2 subsets of myeloid dendritic cells, and a subset of lymphoid dendritic cells. Lymph nodes contain 2 additional subsets representing the mature forms of intestinal tissue: dendritic cells and Langerhans cells. A new class of cells, APC$^{LP}$ cells, has now been identified and classified. APC$^{LP}$ cells share B220 expression with other the dendritic cells. Additional identifying functional features are that APC$^{LP}$ cells express high levels of MHC class II, and do not express CD11c or Gr1. Moreover, APC$^{LP}$ cells are restricted in their distribution in the body to the lamina propria compartment. Thus, APC$^{LP}$ cells are shown to constitute a distinct class of tissue-specific antigen presenting cells that have not been previously known.

The intestinal immune system delicately balances between the induction of tolerance to harmless commensal bacteria and dietary antigens, and the induction of active immunity in the face of pathogens. Probably because the former outnumber the latter, the immune system has a predisposition for tolerance induction. For instance, mesenteric lymph nodes and Peyer's patch cells have a cytokine profile that is dominated by IL-4 and IL-10, and have a generally immunosuppressive environment that can affect new lymphocytes. This may be because of the unusual nature of dendritic cells in Peyer's patch, which elicit suppressive cytokines to stimuli, in contrast to productive cytokines induced by splenic dendritic cells. Moreover, intestinal epithelial cells as well as intra-epithelial lymphocytes produce copious amounts of the potentially immunosuppressive cytokine TGFβ.

Despite the generally suppressive environment, the T cell response to infection is more robust and more prolonged in the intestinal mucosa than in the periphery. This suggests that another level of potent stimulation in the intestinal mucosa may override the normally tolerogenic effects of Peyer's patch and mesenteric lymph node priming, and is consistent with gene expression profiling of intra-epithelial lymphcytes. Accordingly, CD70-mediated costimulation is believed to augment the mucosal response to an oral vaccine, and the lack of such costimulaton is believed to interfere with the excessive mucosal immune response for medical conditions such as inflammatory bowel disease.

Thus, a potentiator of CD70 activity in APC$^{LP}$ cells allows the mucosa to mount an effective immune response to antigen bearing vaccines. In contrast, a suppressor or inhibitor of CD70 activity ameliorates or prevents the initiation of inflammatory conditions such as inflammatory bowel disease.

The CD70 inhibitors of the present invention, when targeted to the gastrointestinal tract using well known techniques, can be used for treating inflammatory conditions such as inflammatory bowel disease, colitis and Crohn's disease. In order to treat diseases and disorder of this type, the CD70 inhibitor can be formulated into a pharmaceutical composition for administration to the subject in a therapeutically effective amount. Typical examples of CD70 inhibitors which can be used in the practice of this invention include CD70 blocking antibodies, CD70-Ig chimeras, small molecule CD70 inhibitors, and CD70 siRNA which for down-regulate CD70 expression. Typical anti-CD70 antibodies are disclosed, for instance, in K. Tesselaar et al., *The Journal of*

*Immunology*, 170: pages 33-40 (2003), the pertinent disclosure of which is incorporated herein in its entirety. As a practical matter, the antibodies can be administered to a suitable subject by iv injection, causing the antibody to bind to the CD70 antigen, introduced in a subject by iv injection.

Figure 1B:
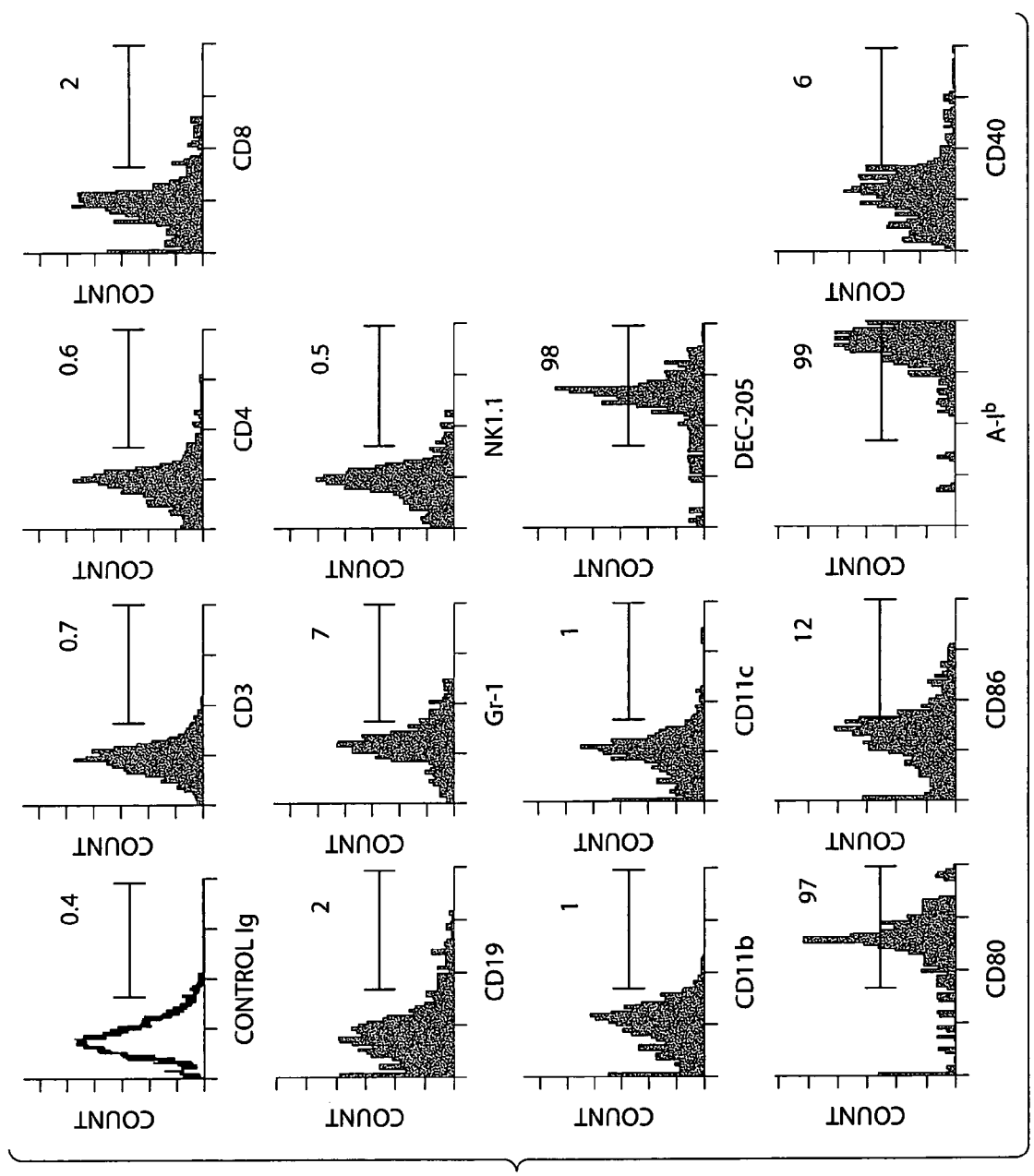
Figure 1C:
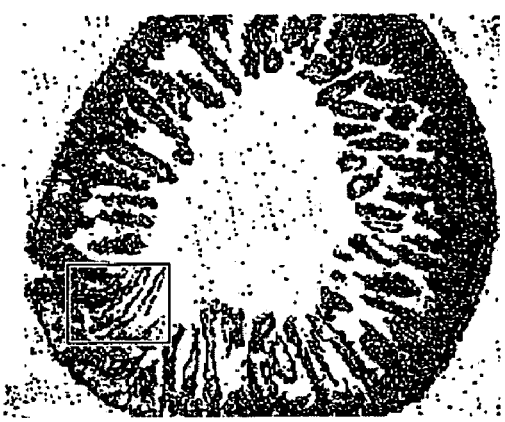
Figure 1C:
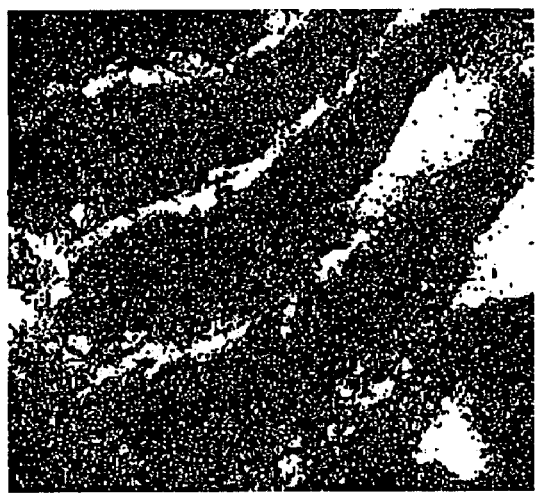
Figure 1C:
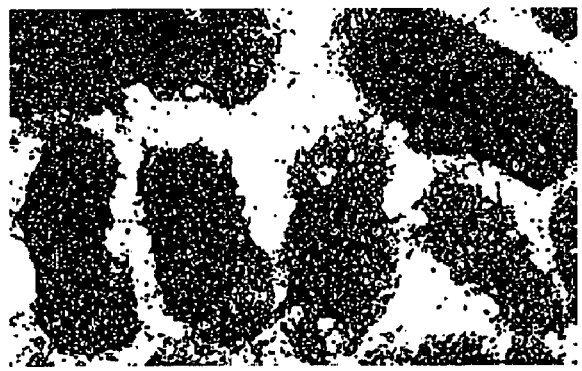

Turning now to the Figures, FIG. 1A is a series of plots showing single cell suspensions from different organs taken from wild type mice examined by flow cytometry for the presence of CD70$^+$ cells. Representative results from more than 10 mice are shown. FIG. 1B are a series of histograms of CD70-gated cells with the percentages shown indicating the expression of different markers. The cells are from the lamina propria compartment phenotyped using the indicated antibodies. FIG. 1C are a series of photomicrographs of intestinal sections stained with anti-CD70 antibody, and examined histologically. Both transverse and longitudinal sections are shown, and the magnifications are indicated.

Figure 2A:
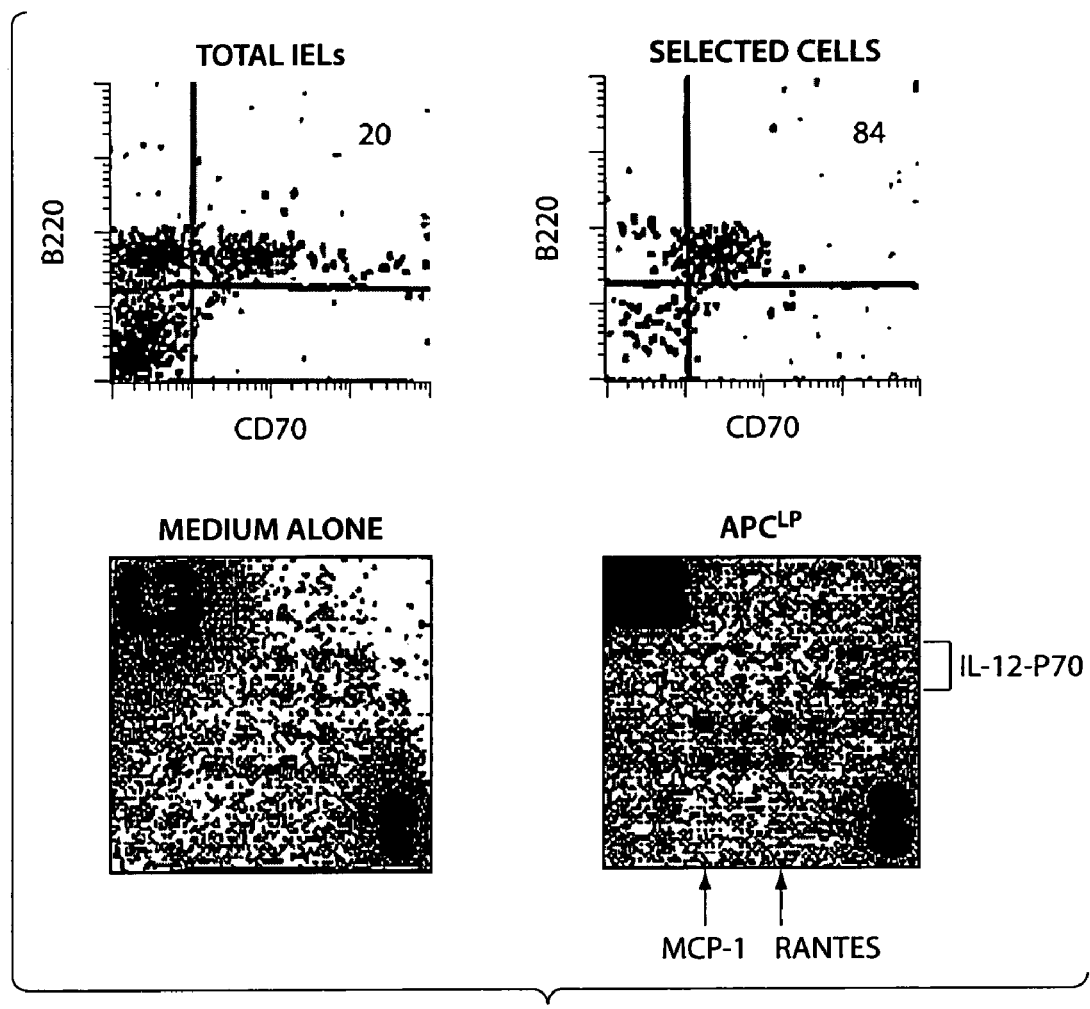
FIGS. 2A-2B illustrate that $APC^{LP}$ cells secrete stimulatory cytokines and stimulate an alloresponse.
Figure 2B:
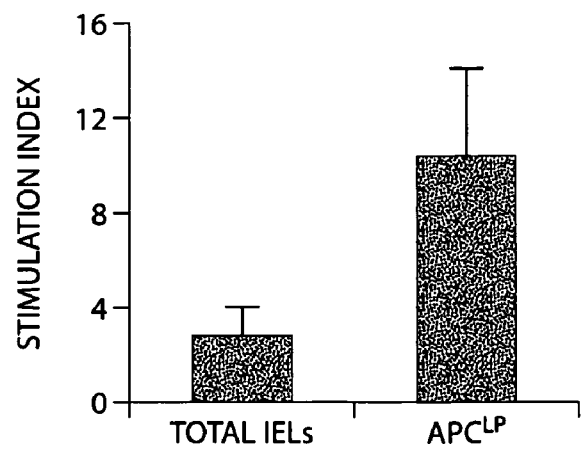

FIG. 2A are pictoral representations of immuno-magnetically isolated APC$^{LP}$ cells taken from C57BL/6 mice evaluated for cytokine production on a mouse cytokine array. FIG. 2B is a bar graph showing APC$^{LP}$ cells cultured with T cells taken from BALB/c mice for 5 days and tested for 3 hours with thymidine incorporation.

Figure 3A:
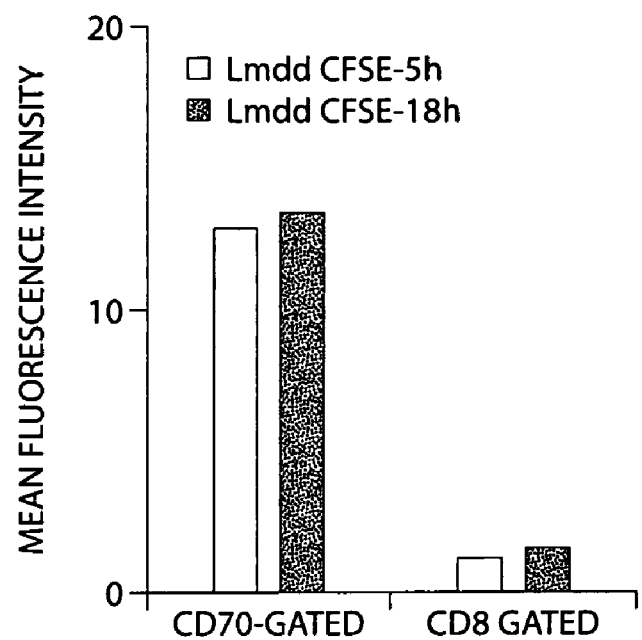
FIGS. 3A-3C illustrate that $APC^{LP}$ cells capture bacteria but do not migrate to Peyer's patch and mesenteric lymph nodes after oral infection.
Figure 3B:
Figure 3C:
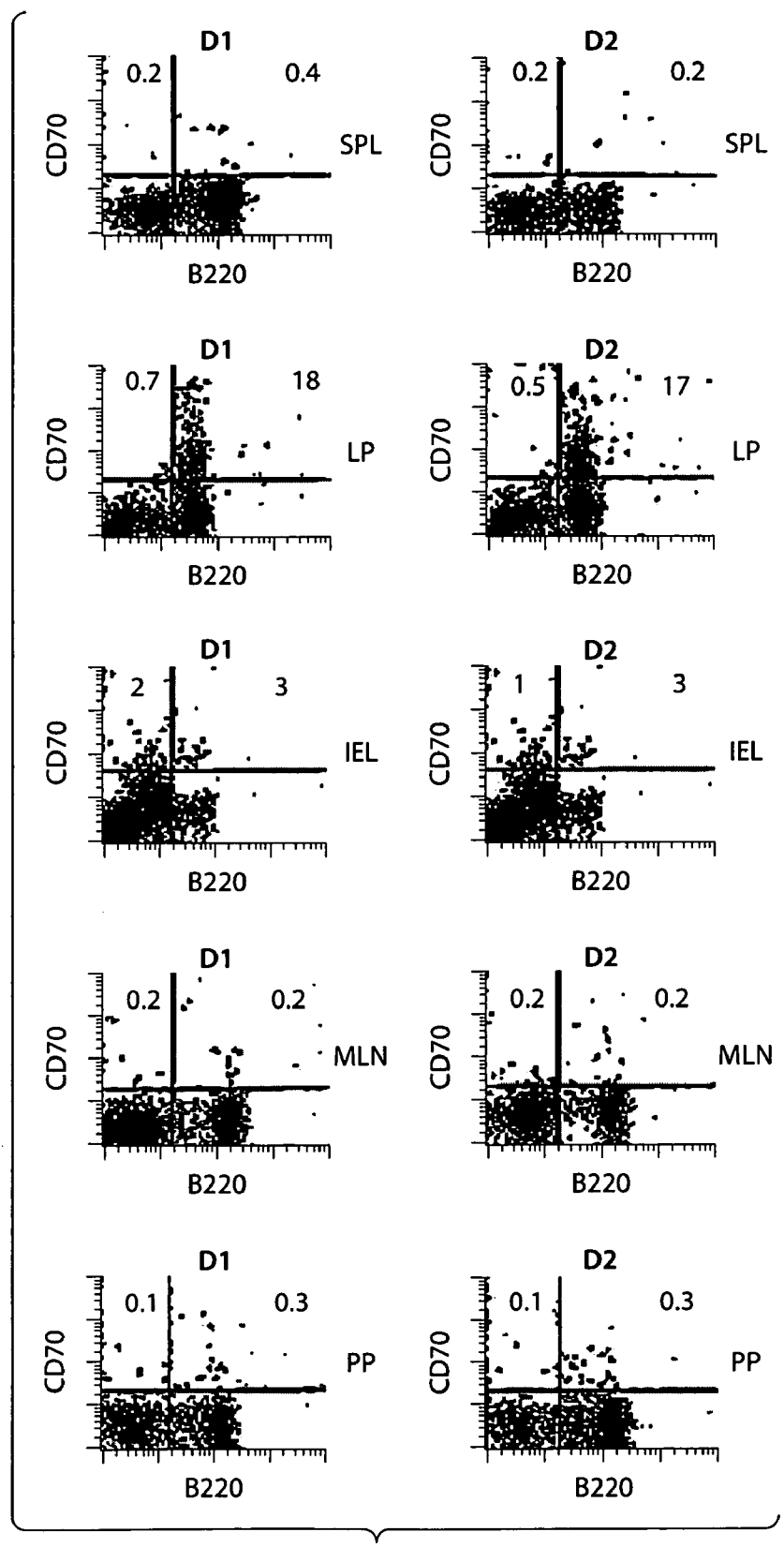

FIG. 3A is a bar graph showing mice orally infected with CSFE (carboxyfluorescein diacetate-succinimidyl ester)-labeled listeria monocytogenes at the indicated times post infection. Intra-epithelial lymphocytes are examined by flow cytometry after staining with CD70 antibody. FL-1 MFI (mean fluorescent intensity) on CD70 or CD8-gated cells from uninfected mice was subtracted from infected mice to calculate specific CSFE flourescence. FIG. 3B is a photomicrograph of the intestinal sections 15 hours post infection stained with CD70 antibody and examined by fluorescence microscopy to visualize CSFE labeled listeria inside CD70$^+$ cells. FIG. 3C are plots of cells from different organs tested for the presence of CD70$^+$ at indicated for times after oral listeria monocytogenes infection.

Figure 4A:
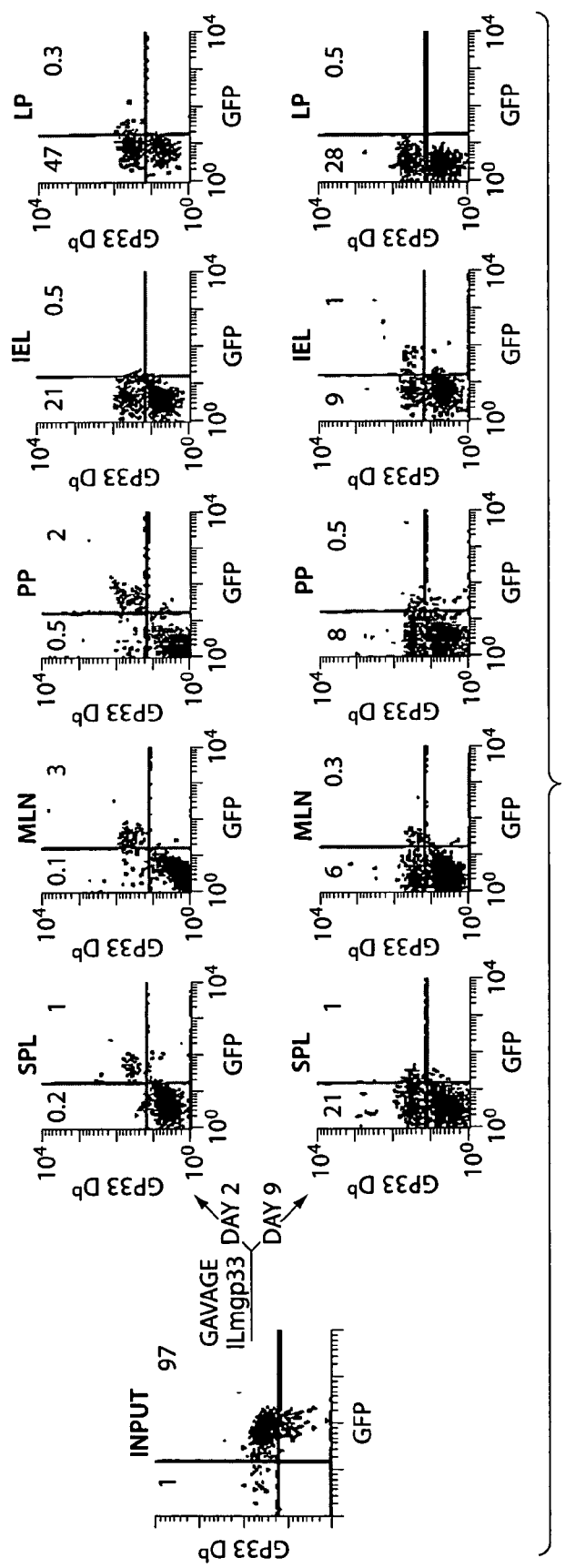
FIGS. 4A-4D illustrate that the expansion and differentiation of T cells occurs in the intestinal mucosa in situ after oral listeria monocytogenes infection.
Figure 4B:
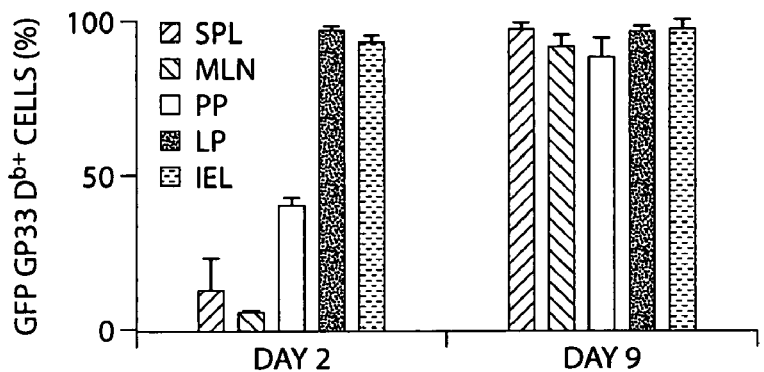
Figure 4C:
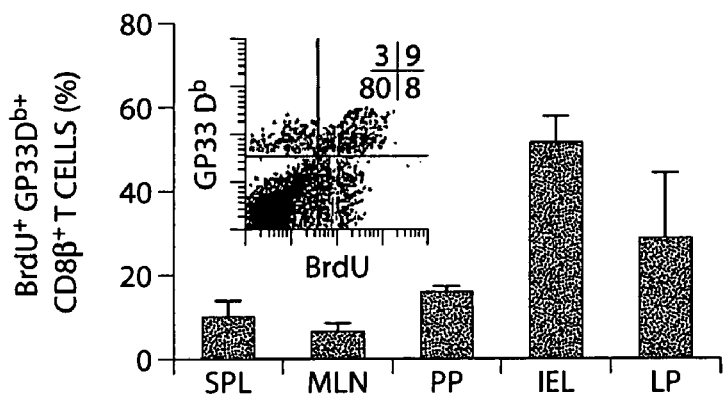
Figure 4D:

FIG. 4A is a series of plots of CD8-gated cells as shown, with the percentages of GFP$^+$ and GFP$^-$ cells as indicated in the plots. Wild type mice adoptively transferred with CD8$^+$ cells from P14$^{T-GFP}$ mice are infected with rLmgp33 by gavage treatment, and at indicated days post infection, cells from different organs are examined by flow cytometry for the presecne of D$^b$GP33 tetramer$^+$ T cells. FIG. 4B is a bar graph showing cumulative data with Standard Deviation ("SD") of loss of GFP expression by D$^b$Gp33 tetramer$^+$ T cells from 6 mice. FIG. 4C is a bar graph showing the effects of dividing DbGp33 tetramer$^+$ T cells in different organs 48 hours after infection, determined by incorporation of BrdU administered 2 hours before harvesting. Data from 4 mice with SD are shown. FIG. 4D is a bar graph showing the frequencies of gp33-specific IFN-γ producing CD8$^+$ T cells in different organs 4 days after oral rLmgp33 infection in wild type mice. Results with SD from 6 mice are shown.

Figure 5A:
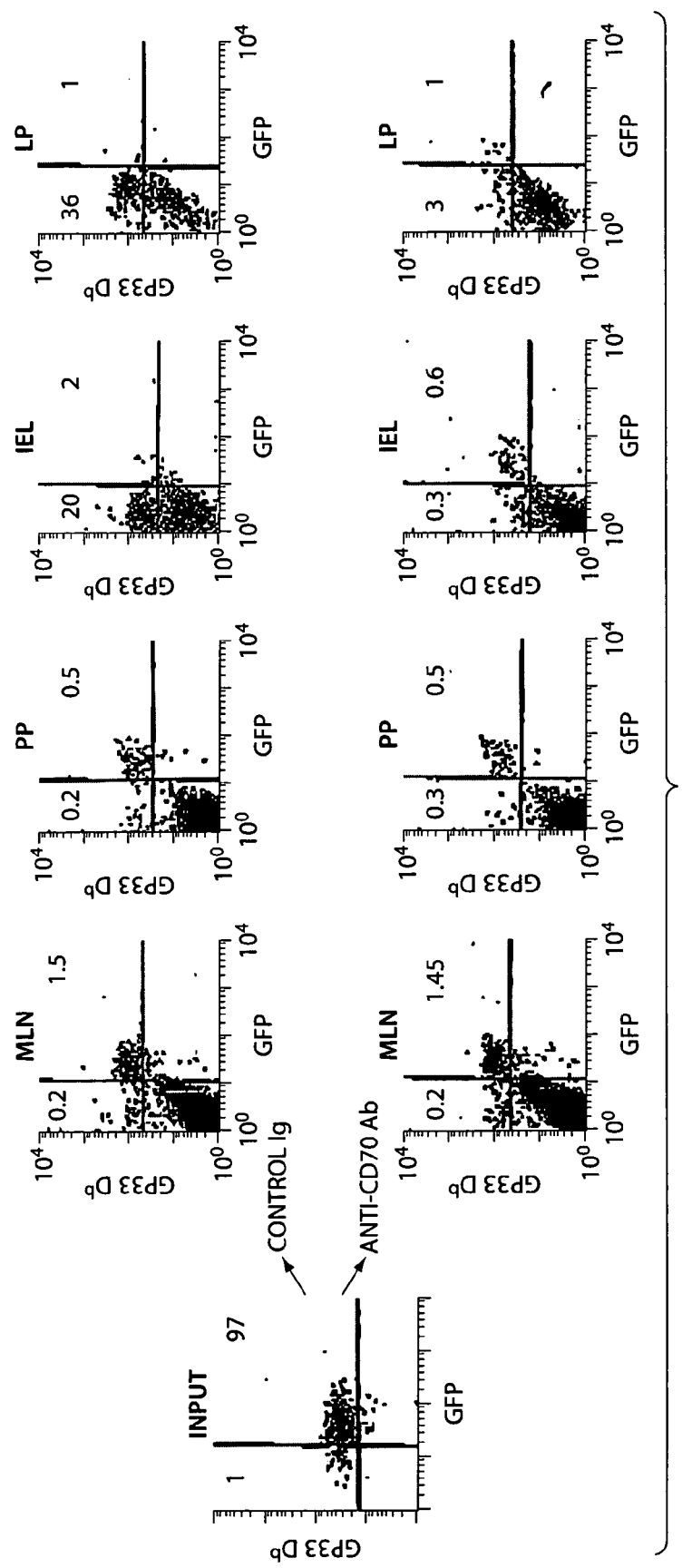
FIGS. 5A-5D illustrate that blocking CD70 antibody treatment abrogates intestinal mucosal T cell response.
Figure 5B:
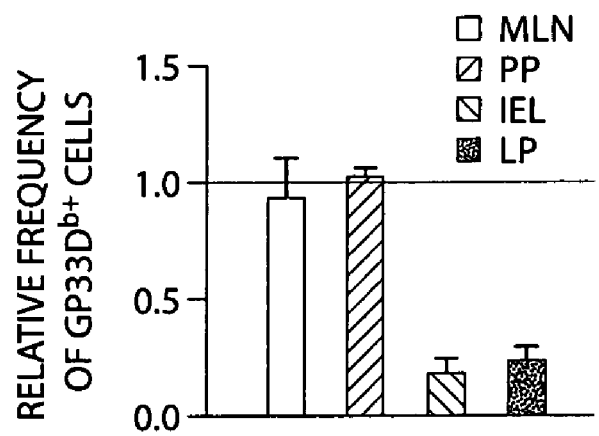
Figure 5C:
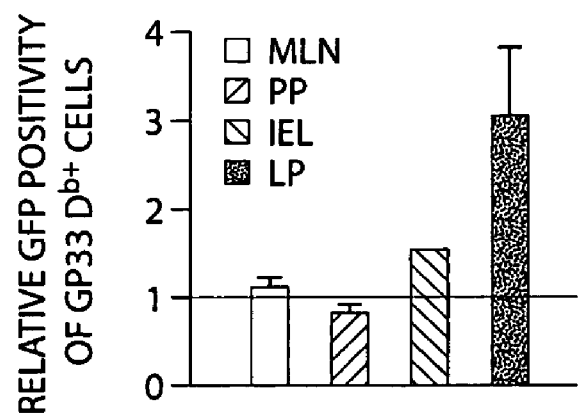
Figure 5D:
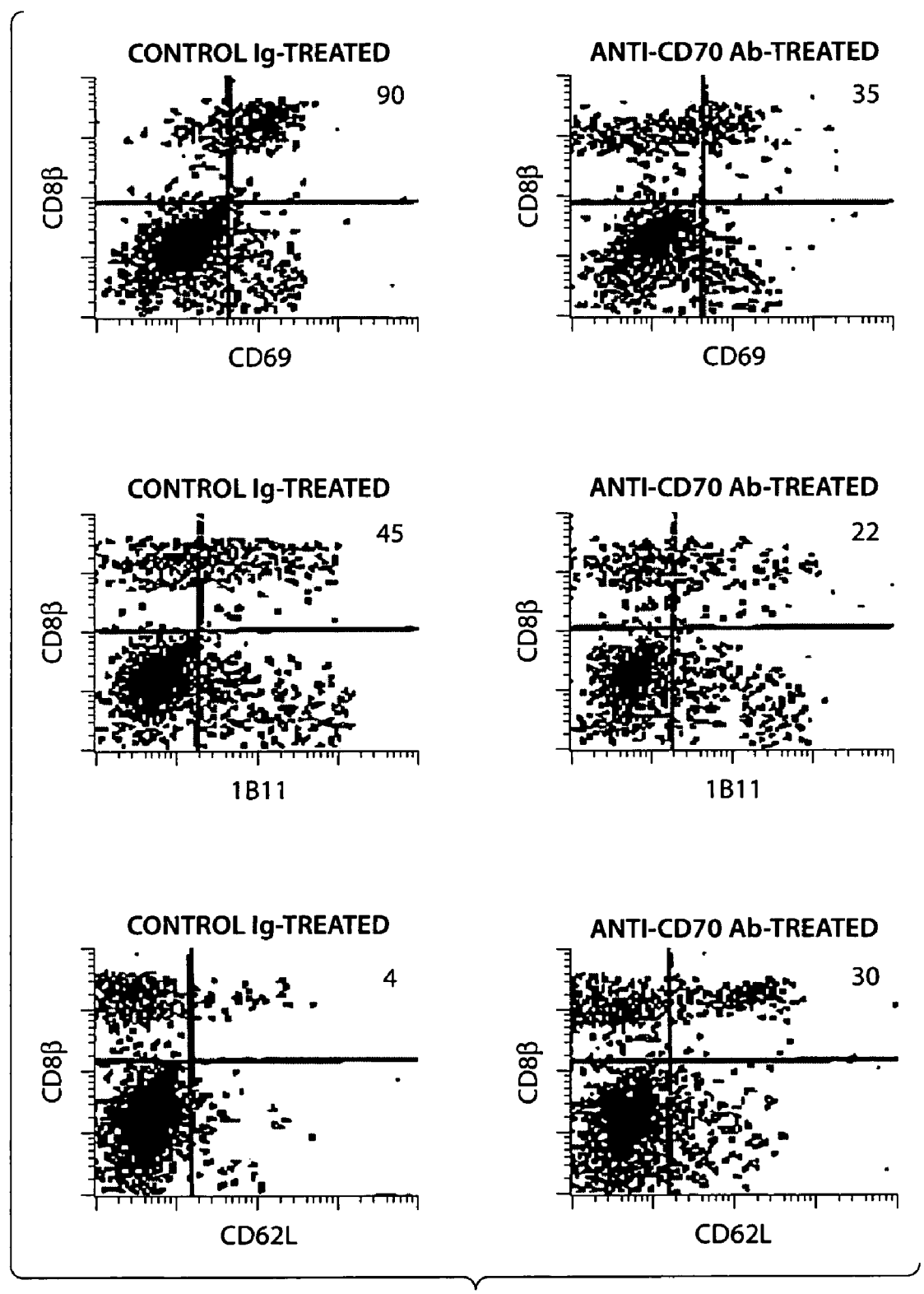

FIG. 5A is a series of photomicrographs showing the percentages of GFP$^+$ and GFP$^-$ cells as indicated. Mice are adoptively transferred with P14$^{T-GFP}$CD8$^+$ cells and infected with rLmgp33 as in FIG. 3. On the day of adoptive transfer and on the day of infection, the mice are also injected iv with 200 μg of control hamster Ig or anti-CD70 antibody. Two days after infection, cells from different organs are examined for the presence of DbGp33 tetramer+ cells. FIGS. 5B and 5C are bar graphs showing cumulative data from 6 mice of tetramer positivity and GFP positivity respectively in anti-CD70 antibody-treated mice relative to control. FIG. 5D is a series of photomicrograhs showing the activation phenotype of resident CD8 T cells in the intra-epithelial lymphopcyte compartment from control and anti-CD70 antibody-treated mice.

Figure 6A:
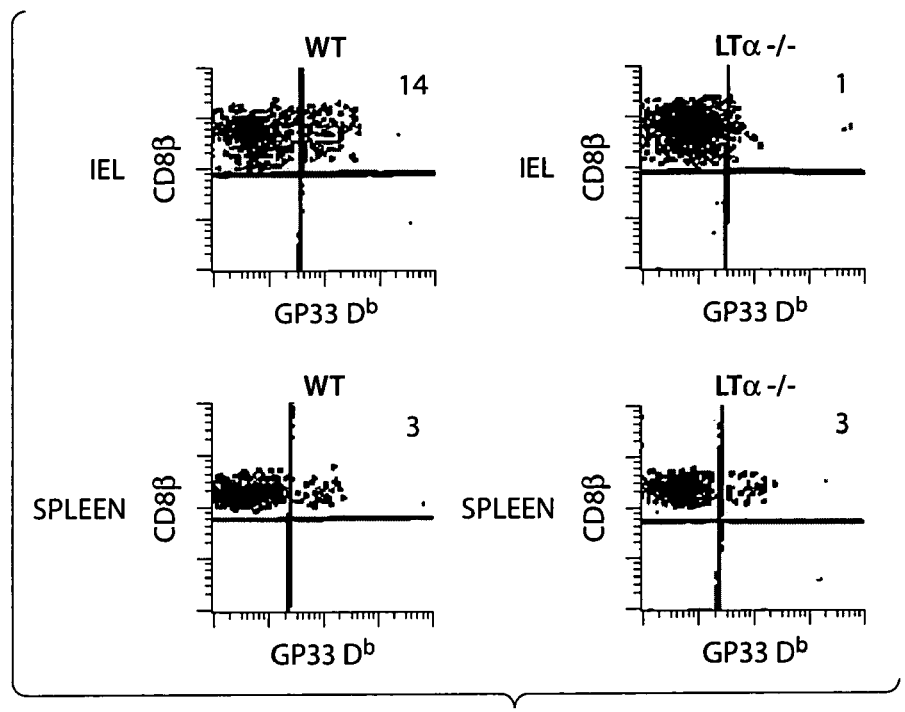
FIGS. 6A-6C illustrate that LTα-deficient mice do not generate an intestinal mucosal T cell response.
Figure 6B:
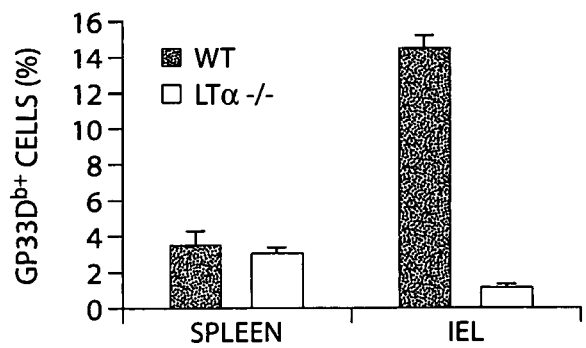
Figure 6C:
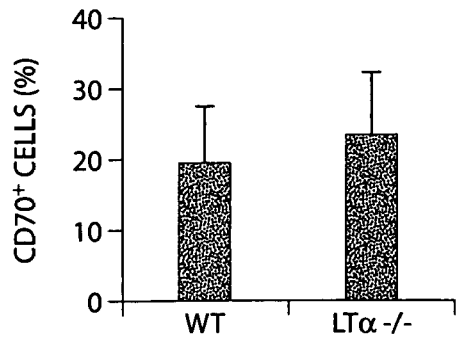

FIG. 6A is a series of photomicrographs showing wild type and LTα$^+$ mice adoptively transferred with P14T-GFPCD8$^+$ cells, and infected with rLmgp33 as in FIG. 3. The lamina propria compartment is examined for the presence of D$^b$Gp33 tetramer$^+$ T cells 2 days later. FIG. 6B is a bar graph showing cumulative data with SD of tetramer positivity in the spleen and the intra-epithelial lymphocyte compartment from 5 mice of each genotype. FIG. 6C shows the frequencies of CD70$^+$ APC$^{LP}$ cells in wild type and LTα$^{-/-}$ mice.

The CD70 inhibitors of this invention can be incorporated into pharmaceutical compositions suitable for administration to a subject. Such compositions typically comprise the inhibitor and a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media, and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

The administration of the active compounds of the invention may be for either a prophylactic or therapeutic purpose. Accordingly, in one embodiment, a "therapeutically effective dose" refers to that amount of an active compound sufficient to result in a detectable change in the physiology of a recipient patient. In one embodiment, a therapeutically effective dose refers to an amount of an active compound sufficient to result in modulation of an inflammatory and/or immune response. In another embodiment, a therapeutically effective dose refers to an amount of an active compound sufficient to result in the amelioration of symptoms of an inflammatory and/or immune system disorder. In another embodiment, a therapeutically effective dose refers to an amount of an active compound sufficient to prevent an inflammatory and/or immune system response.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulation concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Generally, the therapeutically effective amount of the pharmaceutical compositions used herein will vary with the age of the subject and condition, as well as the nature and extent of the disease, all of which can be determined by one of ordinary skill in the art. The dosage may be adjusted by the physician, particularly in the event of any complication. A therapeutically effective amount will typically vary from 0.01 mg/kg to about 1000 mg/kg, preferably from about 0.1 mg/kg to about 200 mg/kg, and most preferably from about 0.2 mg/kg to about 20 mg/kg.

The present invention encompasses active agents which modulate or inhibit CD70 activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

In certain embodiments of the invention, a modulator or inhibitor of CD70 activity is administered in combination with other agents (e.g., a small molecule), or in conjunction with another, complementary treatment regime. Accordingly, the subject may be treated, for example with a CD70 inhibitor, and further treated with an anti-inflammatory or immunosuppressive agent.

The pharmaceutical compositions can be included in a container, pack, or dispenser together with instructions for administration.

The pharmaceutical composition of the invention can include any pharmaceutically acceptable carrier known in the art. Further, the composition can include any adjuvant known in the art, e.g., Freund's complete or incomplete adjuvant. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcohol/aqueous solutions, emulsions or suspensions, including saline and buffered media. Parenteral vehicles include sodium chloride solution, Ringer's dextrose, xylitol, dextrose and sodium chloride, lactated Ringer's solution or fixed oils. Intravenous vehicles include fluid and nutrient replenishers, electrolyte replenishers (such as those based on Ringer's dextrose or xylitol), and the like. Preservatives and other additives may also be present such as, for example, antimicrobials, antioxidant, chelating agents, inert gases and the like.

The pharmaceutical compositions can be administered to the mammal by any method which allows the CD70 inhibitor to reach the appropriate gastrointestinal cells, such as lamina propria cells and intra-epothelial lymphocuytes. These methods include, e.g., injection, infusion, deposition, implantation, oral ingestion, topical administration, or any combination thereof. Injections can be, e.g., by intravenous, intramuscular, intradermal, subcutaneous or intraperitoneal administration. Single or multiple doses can be administered over a given time period, depending upon the progression of the disease, as can be determined by one skilled in the art without undue experimentation. Administration can be alone or in combination with other therapeutic agents. The route of administration will depend on the composition of a particular therapeutic preparation of the invention, and on the intended site of action. The present compositions can be delivered directly to the site of action.

Other delivery systems can include time-release, delayed release or sustained release delivery systems. Such systems can avoid repeated administrations of the active compounds of the invention, thereby increasing the convenience to the subject and the physician. Many types of delayed release delivery systems are available and known to those of ordinary skill in the art. These include polymer-based systems such as polylactic and polyglycolic acid, polyanhydrides and polycaprolactone; nonpolymer systems include lipids such as sterols, and particularly cholesterol, cholesterol esters and fatty acids or neutral fats such as mono-, di- and triglycerides;

hydrogel release systems; silastic systems; peptide based systems; wax coatings, compressed tablets using conventional binders and excipients, partially fused implants and the like. In addition, pump-based hardware delivery systems can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above.

With regard to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Pharmacogenomics thereby allows a clinician or physician to target prophylactic or therapeutic treatments to patients who will most benefit from the treatment and to avoid treatment of patients who will experience toxic drug-related side effects.

The CD70 inhibitors of this invention can be prepared or obtained by methods and techniques well known to those skilled in the art. For example, CD70 monoclonal antibodies can be prepared as described in detail in K. Tesselaar et al., *The Journal of Immunology*, 170: pages 33-40 (2003), the pertinent disclosure of which is incorporated by reference herein in its entirety. Suitable CD70 inhibitors can also be obtained through the use of screening assays, such as high-throughput screening assays, which can be used to identify candidate CD70 inhibitors expressed by the APC$^{LP}$ cells. Accordingly, a library of potentially active compounds can be prepared, and suitable inhibitory compounds contained within the library can be identified. The library can be constructed to include compounds which are targeted to the CD70 antigen expressed by the APC$^{LP}$ cells to identify biologically active agents.

This invention is further illustrated by the following examples which should not be construed as limiting. The contents of all references, patents and published patent applications cited throughout this application, are incorporated herein by reference.

EXAMPLE 1

Materials and Methods

Mice

C57BL/6 and BALB/c mice were purchased from the Jackson Laboratory (Bar Harbor, Me.). T-GFP Tg mice, backcrossed to C57BL/6 mice for 7 generations, were bred into P14 TCR-Tg mice, specific for the LCMV gp33-41 peptide, that had been extensively backcrossed to C57BL/6 mice (N10) to derive P14$^{T-GFP}$ mice. See Manjunath, N. et al., *Proc. Natl. Acad. Sci. U.S.A.*, 96, 13932-13937 (1999), and Pircher, H. et al., *Nature*, 342, 559-561 (1989). LTα-deficient mice used herein are described in De Togni, P. et al., *Science*, 264, 703-707 (1994). All mice were maintained under specific pathogen-free (SPF) conditions in microisolater cages, and were used when they were 6-10 weeks of age.

Adoptive Transfer

Naïve CD8$^+$ T cells were purified from splenocytes of P14 or P14$^{T-GFP}$ mice by negative selection using the murine T cell CD8 subset isolation kit (R&D systems, Minneapolis, Minn.) according to the manufacturer's instructions. The isolated cells were greater than 90% pure. C57BL/6 recipient mice were injected iv with 5×10$^6$ purified CD8$^+$ T cells.

Oral Infection with Listeria Monocytogenes

Mice were infected by gavage with 10$^9$ CFU of recombinant listeria monocytogenes encoding the LCMV glycoprotein (rLmgp33), and at indicated times post infection, their spleen, mesenteric lymph nodes, Peyer's patch and intestine were harvested. In some experiments, mice were gavaged with a highly attenuated D-alanine-deficient listeria mono-Cytogenes strain that was labeled with 1 µM carboxyfluorescein diacetate-succinimidyl ester (CFSE). See Lieberman, J. et al., *Vaccine*, 20, 2007-2010 (2002).

Isolation of Lymphocytes from Peyer's Patch, Lamina Propria and Intra Epithelial Lymphocyte Compartment Intestinal lymphocytes were isolated as described in Lefrancois, L. et al., *Current Protocol Immunology*, 3.19, 1-16 (1996). Briefly, the intestine was flushed with 20 ml PBS, and Peyer's patch was excised, and the intestine was cut longitudinally along its entire length. After 3 washes, the intestine was cut into small pieces, transferred to a 50 ml tube in 20 ml HBSS containing 2% FBS and 1 mM EDTA, and shaken in an incubator at 37° C. for 20 minutes. The supernatant was harvested, the EDTA treatment was repeated 2 more times, and intra-epithelial lymphocytes were isolated from the pooled supernatants. Finally, the intestinal pieces were digested with 50 U/ml of collagenase (type VIII, Sigma) with shaking at 37° C. for 30 minutes. Lamina propria lymphocytes were isolated from the supernatants. Both the intra-epithelial lymphocytes and lamina propria lymphocytes were washed 2 times in PBS, suspended in 8 ml of 44% percoll, layered on 5 ml of 67% percoll, and centrifuged for 20 minutes at 600×g. The interface cells were collected, washed and stained with various antibodies for flow cytometric analysis.

Flow Cytometric Analysis

MHC D$^b$/gp33 tetramers were obtained from Beckman Coulter Immunomics, San Diego, Calif. Anti-mouse DEC 205-FITC was obtained from Research Diagnostics, Flanders, N.J. FITC, PE or Cy-5 conjugated antibodies to mouse CD4, CD8, CD11a, CD11b, CD11c, CD19, CD40, CD70, CD80, CD86, B220, Gr-1, NK1.1, and I-A, were obtained from BD PharMingen, San Diego, Calif. Blocking anti-CD70 antibody is described in Tesselaar, K. et al., *Nat. Immunol.*, 4, 49-54 (2003). Immmunostaining and flow cytometric analysis were done as described in Manjunath, N. et al., *J. Clin. Invest.*, 108, 871-878 (2001).

Immunomagnetic Isolation, Allogenic Stimulation and Cytokine Assay

Intra-epithelial lymphocytes from C57BL/6 mice were first stained with CD19-coated Miltenyi beads, and the B cells were depleted using a Miltenyi miniMACS system. The cells were subsequently stained with B200-coated Miltenyi beads to positively select B220$^+$ APC$^{LP}$ cells. The isolated cells were greater than 80% pure for APC$^{LP}$ cells as assessed by staining with CD70 antibody. To generate an allorepsonse, $10^3$ of APC$^{LP}$ cells from C57BL/6 mice were irradiated (4000 rads) and cultured for 5 days with $10^5$ T cells (purified using R&D systems T cell enrichment columns) from BALB/c mice in triplicate in 96 well plates, pulsed with $^3$H thymidine (0.5 μci/well) for 6 hours, harvested and counted for thymidine incorporation using a Packard Topcount harvester and a microplate reader.

Cytokine production by isolated APC$^{LP}$ cells was tested using a mouse cytokine assay kit (Raybiotech, Inc., Norcross, Ga.) according to the manufacturer's instructions. Briefly, $10^5$ APC$^{LP}$ cells were incubated in 1 ml of conditioned medium over the array membrane for 10 hours, following which the membrane was washed, incubated with biotin-conjugated antibodies developed using HRP-conjugated stretavidin, and exposed to Kodak x-omat film for 1 min.

ELISPOT Assay

ELISPOT assays were done in Millipore HA platelets (Millipore, Bedford, Mass.), and coated with anti-mouse IFN-γ (AN-18, BD Pharmingen). Single cell suspensions from different organs were plated in cells containing gp33-41 peptide, KAVYNFATC (SEQ ID NO:1)(5 μg/ml, synthesized at BioSource, Calif.) pulsed or unpulsed MC57G cells. Cytokine production was detected after 24 hours using biotinylated antibody against IFN-γ (R4-6A2, BD Pharmingen), followed by contact with alkaline phosphatase-conjugated antibiotin monoclonal antibody (Vector Laboratories, Burlingame, Calif.), and precipitated alkaline phosphatase substrate, nitroblue tetrazolium-5-bromo-4-chloro-3-indolylphosphate (Pierce, Rockford, Ill.). Spots were counted using a digital imager and Immunospot software (version 3, Cellular Technology, Ltd., Cleveland, Ohio). The number of spots was normalized with respect to CD8β$^+$T cells (determined in parallel by flow cytometry) to give a final result as the number of spot-forming cells per $10^4$ cells.

BrdU Incorporation Assay

In vivo BrdU labeling (see below) was done as described in Meyer, A. L. et al., *Journal=l of Immunology*, 166, 5773-5781 (2001). Two hours before sacrifice, mice were injected ip with 1 ml of BrdU (1-bromo-2' deoxyuridine and 5-fluoro-2' deoxyuridine) labeling reagent (Zymed, South San Francisco, Calif.) per 100 g body weight. Lymphocytes harvested from various organs were stained externally with anti-mouse CD8 Cy-5 and gp33 tetramer PE, fixed, permeabilized and stained internally with anti-BrdU FITC as described in Manjunath, N. et al., *J. Clin. Invest.*, 108, 871-878 (2001).

Immunohistology

Intestinal tissue was embedded in O.C.T. medium and snap-frozen in liquid nitrogen. Eight micron cryostat sections were either reacted with anti-CD70 mAb followed by goat anti-rat Ig TRITC and examined by Leica DM LB fluorescent microscope, or reacted with anti-CD70 mAb followed by goat anti-rat HRP and Nova Red substrate (Vector Laboratories, Burlingame, Calif.), and counter stained with 1% Methyl Green for examination with a light microscope.

EXAMPLE 2

Presence of an Unusual Type of Dendritic-like Cells in the Intestinal Mucosa

The constitutively activated phenotype and function of T cells in the intestinal mucosa is reminiscent of the persistent activation of T cells seen in CD70 Tg mice. CD70 expressing cells were tested to determine whether the cells are present in the intestinal mucosa in naïmice. A substantial portion of cells in the lamina propria compartment, but not in the other tissues tested, including Peyer's patch and mesenteric lymph nodes, were found to express CD70 as shown in FIG. 1A.

Surface CD70 antigen is expressed by activated B cells, mature dendritic cells, and to a lesser extent, T cells. The CD70 expressing cells were phenotyped in lamina propria in detail (see FIG. 1B). These cells were negative for CD3, CD4 or CD8 expression, indicating that they are not of T cell origin. The cells expressed B220, but were not B cells because they were CD19 negative. The cells also did not express the NK1.1 or Gr-1 molecules. However, the cells reacted strongly with DEC205, suggesting that they may be of dendritic cell origin. Several dendritic cell subsets have been detected in the mouse Peyer's patch and the lamina propria layer based on CD11c, CD11b and DEC205 expression. Therefore, the presence of these markers was also evaluated. The CD70$^+$ cells did not express CD11c or CD11b, but expressed high levels of MHC Class II and the costimulatory molecule, CD80. However, the cells were negative for CD40 and CD86 (see FIG. 1B). These results suggest that the lamina propria contains an unusual population of dendritic cell-like cells that express B220, DEC205, MHC Class II, and the costimulatory moleucles CD80 and CD70. Upon immunohistological examination of intestinal sections, the CD70$^+$ cells were seen to be localized exclusively beneath the villous epithelium (see FIG. 1C). The abundance of these cells was striking in that they appeared to line up with the entire length of the villus epithelium.

EXAMPLE 3

Antigen Presentation and Cytokine Secretion by APC$^{LP}$ Cells

APC$^{LP}$ cells were tested to determine whether these cells have antigen-presenting ability. Lamina propria cells from C57BL/6 mice (H-2$^b$) were first immunomagnetically depleted of B cells after staining with CD19 antibody, and the remaining cells were then stained with B220 antibody to positively select B220$^+$ APC$^{LP}$. The isolated cells were greater than 80% enriched for APC$^{LP}$ cells as assessed by staining with CD70 antibody. The ability of these cells to stimulate purified T cells from BALB/c mice (H-2$^d$) was assessed. As shown in FIG. 2A, the APC$^{LP}$ cells were able to stimulate a potent alloresponse.

The cytokine secretion ability of APC$^{LP}$ cells was also evaluated. Cytokine production by immunomagnetically isolated APC$^{LP}$ cells was tested using a RayBio Mouse Cytokine Array I kit, which allows simultaneous detection of 22 cytokines at the protein level. As shown in FIG. 2B, ex vivo isolated APC$^{LP}$ cells from normal mice were capable of producing copious amounts of cytokines associated with immunostimulatory dendritic cells, including bioactive IL12p70, MCP-1 and RANTES, but not suppressive IL-10 or IL-4. Thus, APC$^{LP}$ cells were found to be capable of presenting antigen effectively and secreting T cell stimulatory cytokines. These results also indicate that APC$^{LP}$ cells are constitutively activated in the intestinal mucosa, probably due to continuous exposure to environmental antigens.

EXAMPLE 4

In Vivo Bacterial Uptake by $APC^{LP}$ Cells $APC^{LP}$ cells were tested to determine whether these cells were capable of taking up antigen in vivo. Mice were orally infected with CFSE labeled listereia monocytogenes. Because CSFE gets diluted with bacterial replication, a strain of D-alanine-deficient listeria that is incapable of replication in the absence of externally supplemented D-alanine was used. After 5 hours and 18 hours of infection, $APC^{LP}$ cells, but not CD8 T cells, were seen to acquire green fluorescence by flow cytometric analysis of isolated lamina propria cells (see FIG. 3A). The presence of CSFE labeled listeria inside $CD70^+$ cells was also confirmed by flourescence microscopy of intestinal sections (see FIG. 3B).

It has been suggested that dendritic cells can pick up antigen in the mucosa and migrate to Peyer's patch and mesenteric lymph nodes to prime T cells. Moreover, CD70, which is not expressed by any cell types in vivo in naïve mice, can be expressed on a small (5%) fraction of lung infiltrating T cells 6-8 days after intranasal infection with influenza virus. Thus, to determine if $APC^{LP}$ cells can migrate to Peyer's patch and mesenteric lymph nodes, and to test if CD70 is induced on T cells after an oral infection, various organs were tested for the presence of CD70 expressing cells 1 and 2 days after an oral infection with listeria monocytogenes. Under these conditions, an enhanced number of CD70 expressing cells were seen in the lamina propria compartment, but no CD70 expressing cells of any kind were found in any other organs, including the draining mesenteric lymph nodes and Peyer's patch (see FIG. 3C). Thus, CD70 expression in vivo is confined to $APC^{LP}$ cells, and $APC^{LP}$ cells do not migrate to Peyer's patch and mesenteric lymph nodes after listeria monocytogenes infection.

EXAMPLE 5

In Situ Expansion and Differentiation of T Cells in the Intestinal Mucosa

The presence of a unique population of antigen presenting cells in the lamina propria compartment suggested that these cells might be involved in T cell stimulation in situ. To test this hypothesis, the expansion of adoptively transferred P14 TCR transgenic $CD8^+$ T cells (specific for LCMV glycoportein) in the intestinal mucosa was compared with that in Peyer's patch, mesenteric lymph nodes and spleen after oral challenge with recombinant listeria expressing LCMV glycoprotein (rLmgp33). For these studies, $CD8^+$ T cells from the P14 TCR Tg mice crossed to T-GFP mice ($P14^{T-GFP}$) were used. In T-GFP mice, GFP uniformly expressed in naïand early activated $CD8^+$ T cells is selectively turned off once the cells differentiate into phenotypically and functionally mature cytotoxic effector T cells, and thus the loss of GFP expression provides a simple marker to identify fully differentiated effector T cells. Thus, the $P14^{T-GFP}$ system allows identification of antigen-specific cells by gp33 tetramer staining, and simultaneously assessing their differentiation status by GFP expression.

Purified $CD8^+$ T cells from $P14^{T-GFP}$ mice were adoptively transferred to C57 recipients, and after 4 days the mice were infected orally with rLmgp33. Different organs were tested for the presence of gp33 tetramer binding donor-derived $CD8^+$ T cells by flow cytometry on days 2 and 8 after infection. As shown in FIG. 4A, a major expanded population of tetramer positive $CD8^+$ T cells was present only in the intra-epithelial lymphocyte layer and the lyhmphoid peripheral tissues on day 2-post infection, constituting between 20% and 40% of $CD8^+$ T cells, whereas these cells constituted less than 2% in Peyer's patch and mesenteric lymph nodes. This represents about a 2 fold increase over adoptively transferred, uninfected mice for Peyer's patch and mesenteric lymph nodes, and greater than a 50 fold increase for the intra-epithelial lymphocytes (not shown in the Figures). Moreover, while the majority of tetramer positive cells in the secondary lymphoid organs were $GFP^+$, those in the lamina propria and intra-epithelial lymphocyte compartment were uniformly $GFP^-$ (see FIG. 4B), indicating that the tetramer positive cells had differentiated into full-fledged effector T cells in the intestinal mucosa. However, on day 8-post infection, expansion of GFP-tetramer$^+$ P14 cells was readily detectable in all organs. Thus, the major expansion and differentiation of antigen-specific T cells occurs first in the intestinal mucosa in situ. Whether the expanded tetramer$^+$ cells seen in the secondary lymphoid organs on day 8 represent delayed activation in these organs or seeding by recirculation of mucosal T cells is unclear.

To test if the increased numbers of transferred cells seen on day 2 post infection in the intra-epithelial lymphocyte and lamina propria is due to an accumulation of dividing cells migrating from the mesenteric lymph nodes and Peyer's patch, or represent in situ proliferation, in vivo Bromo deoxy Uridine (BrdU) labeling studies were also performed. Mice were adoptively transferred with P14 (not $P14^{T-GFP}$) $CD8^+$ cells, and infected with rLmgp33. Two days later, BrdU was injected iv, and after 2 hours, the mice were sacrificed and the presence of BrdU+ cells in different organs was determined by flow cytometry. As shown in FIG. 4C, about 50% of gp33 tetramer$^+$ cells in the intra-epithelial lymphocyte compartment, and approximately 25% of cells in the lamina propria layer, were BrdU$^+$, whereas only 10-15% of cells in the mesenteric lymph nodes and Peyer's patch incorporated BrdU. Thus, antigen-specific T cells were actively replicating in the intestinal mucosa in situ.

Because unnatural numbers of CTLp that are present in the adoptive transfer system may not accurately represent normality, the question of whether indogenous CTLs also expand first in the mucosa following oral listeria monocytogenes infection was evaluated. C57 mice were infected by gavage with rLmgp33, and the frequency of gp33-49 peptide-specific IFN-γ producing $CD8^+$ T cells in various organs was compared on days 2 and 4 after infection in an ELISPOT assay. Unlike the adoptive transfer system, significant levels of IFN-γ producing cells were not seen in any organ on day 2 post infection (not shown in the FIGS.). However, high frequencies of gp33-specific IFN-γ producing CD8 T cells could be found in the intra-epithelial lymphocyte compartment, but not other organs on day 4 post infection. Thus, although the kinetics is faster in the adoptive transfer system because of excessive precursor numbers, the T cell activation pattern reflects what occurs in a natural infection. Taken together, the results show that the major site for expansion and differentiation of antigen-specific CTL following oral listeria infection is the intestinal mucosa itself.

EXAMPLE 6

CD70 Blocking Prevents Intestinal Mucosal T Cell Expansion

In CD70 Tg mice, the profound expansion of effector-memory T cells is dependent on continuous CD27-CD70 interaction, and CD blocking antibody treatment can effectively reverse the phenotype to wild type levels. Thus, to test the importance of CD70-mediated costimulation via APC$^{LP}$ cells in antigen-specific T cell expansion, the question of whether the mobilization of adoptively transferred P14$^{T\text{-}GFP}$ cells after oral listeria monocytogenes infection can be blocked by anti-CD70 antibody was evaluated.

Anti-CD70 antibody was administered on the day of adoptive transfer and repeated on the day of infection 4 days later. This treatment was enough to abrogate P14$^{T\text{-}GFP}$ cell expansion seen on day 2 post infection in lamina propria cells and the intra-epithelial lymphocytes of control mice (see FIG. 5A). The effect of CD70 antibody treatment was specific to intra-epithelial lymphocytes and lamina propria cells, and did not affect the limited T cell expansion in the Peyer's patch and mesenteric lymph nodes (see FIG. 5B). Moreover, in contrast to control antibody-treated animals where the tetramer$^+$ cells had completely lost GFP expression, the few cells present in the intra-epithelial lymphocytes and lamina propria cells of anti-CD70 treated mice retained GFP expression (see FIG. 5C), indicating that although P14$^{T\text{-}GFP}$ cells were able to reach the intestinal mucosa, they were unable to proliferate and differentiate to effector cells. Thus, costimulation mediated by CD70 is required for antigen-specific T cell expansion in the intestinal mucosa. Because CD70 is expressed only on APC$^{LP}$ cells and not on other cells in the intestinal mucosa, nor on any cells in Peyer's patch or mesenteric lymph nodes (see FIG. 3C), these results suggest a pivotal role for APC$^{LP}$ cells in the induction of T cell expansion and differentiation in the mucosa.

T cells in the intestinal mucosa exhibit constitutively activated phenotype and function, probably due to stimulation with intestinal-associated environmental antigens. Since CD70-mediated costimulation via APC$^{LP}$ cells is involved in antigen-specific T cell expansion during an infection, the effect of blocking CD70 on resident T cells in normal uninfected mice was tested.

Wild type mice were injected iv with either control Ig or anti-CD70 antibody on day 0 and day 4, and the phenotype of CD8$^+$ T cells was determined 3 days following the second injection. As FIG. 5D shows, there was a marked reduction in the expression of the early activation marker, CD69, and the effector T cell marker, CD43 isoform recognized by the monoclonal antibody 1B11. Conversely, L-selectin down-modulation seen in control Ig-treated mice was significantly reduced in the anti-CD70 antibody-treated mice. Thus, it is appropriate to conclude that APC$^{LP}$ cell control T cell activation and differentiation in the intestinal mucosa, regardless of antigen-specificity.

EXAMPLE 7

Lack of Intestinal Mucosal T Cell Expansion in LTα$^{-/-}$ Mice

Since the intestinal mucosa may be the site where the T cell expansion and differentiation occurs in a CD70-dependent fashion, this example addresses where the initial priming of T cells occurs.

To determine if Peyer's patch and mesenteric lymph nodes are required to generate a T cell response during listeria infection, the expansion of adoptively transferred P14 cells following rLmgp33 infection in wild type and LTα-deficient mice that lack Peyer's patch and lymph nodes were compared. Although the spleens in both groups contained equivalent numbers of tetramer cells, the expansion of tetramer cells in the intra-epithelial lymphocytes seen in wild type mice was dramatically reduced in the LTα$^{-/-}$ mice (see FIGS. 6A and 6B). However, the LTα$^{-/-}$ mice had similar levels of CD70$^+$ APC$^{LP}$ cells as compared to wild type mice (see FIG. 6C). These results suggest that Peyer's patch and/or mesenteric lymph nodes are required for initial T cell priming following listeria infection. However, it is possible that defects in expression of chemokines and adhesion molecules in the LTα$^{-/-}$ mice, by impairing intestinal homing of transferred cells, may have contributed to the defects in T cell expansion observed in the LTα$^{-/-}$ mice.

A number of embodiments of the invention have been described herein. Nevertheless, it will be understood that various modifications may be made to the invention without departing from its spirit and scope. Accordingly, embodiments other than those specifically described herein are intended to be embraced by the following claims. Those skilled in the art will be able to ascertain, using no more than routine experimentation, many equivalents of the specific embodiments of the invention described herein. These and all other equivalents are intended to be encompassed by the following claims.

---

What is claimed is:

1. A method for treating a subject having the symptoms of inflammatory bowel disease comprising administering to the lamina propria antigen presenting cells of the intestinal mucosa of a subject a pharmaceutical composition comprising an effective amount of an inhibitor for CD70, said inhibitor being a CD70 blocking antibody.

2. The method of claim 1 wherein the pharmaceutical composition includes a pharmaceutically acceptable carrier and an adjuvant.

3. The method of claim 1 which is used as an adjunct to another therapeutic treatment.

* * * * *